United States Patent
Gong et al.

(10) Patent No.: US 9,815,848 B2
(45) Date of Patent: Nov. 14, 2017

(54) METHOD FOR PREPARING SPHERICAL CLOPIDOGREL HYDROGEN SULFATE POLYMORPH I

(71) Applicants: SHENZHEN SALUBRIS PHARMACEUTICALS CO., LTD, Shenzhen (CN); Tianjin University, Tianjin (CN)

(72) Inventors: Junbo Gong, Tianjin (CN); Qi Wang, Tianjin (CN); Qiuxiang Yin, Tianjin (CN); Jingkang Wang, Tianjin (CN); Xiaopeng Song, Tianjin (CN); Baohong Hou, Tianjin (CN); Liting Liao, Shenzhen (CN); Duanming Tan, Shenzhen (CN); Ziyuan Di, Shenzhen (CN)

(73) Assignees: TIANJIN UNIVERSITY, Tianjin (CN); SHENZHEN SALUBRIS PHARMACEUTICALS CO., LTD, Shenzhen (CN)

(*) Notice: Subject to any disclaimer, the term of this patent is extended or adjusted under 35 U.S.C. 154(b) by 0 days.

(21) Appl. No.: 15/302,944

(22) PCT Filed: Dec. 31, 2014

(86) PCT No.: PCT/CN2014/095926
§ 371 (c)(1),
(2) Date: Oct. 7, 2016

(87) PCT Pub. No.: WO2016/011783
PCT Pub. Date: Jan. 28, 2016

(65) Prior Publication Data
US 2017/0037054 A1    Feb. 9, 2017

(51) Int. Cl.
*C07D 495/04* (2006.01)
*A61K 31/425* (2006.01)
*A61K 31/4743* (2006.01)

(52) U.S. Cl.
CPC .......... *C07D 495/04* (2013.01); *A61K 31/425* (2013.01); *A61K 31/4743* (2013.01); *C07B 2200/13* (2013.01)

(58) Field of Classification Search
CPC .................................................. C07D 495/04
USPC ........................................................ 546/114
See application file for complete search history.

(56) References Cited

U.S. PATENT DOCUMENTS

| | | | |
|---|---|---|---|
| 6,767,913 B2 * | 7/2004 | Lifshitz | C07D 495/04 514/301 |
| 7,629,465 B2 * | 12/2009 | Kumar | C07D 495/04 546/114 |
| 7,772,398 B2 | 8/2010 | Sajja et al. | |
| 2005/0059696 A1 | 3/2005 | Reddy et al. | |
| 2012/0232274 A1 * | 9/2012 | Burger | C07D 495/04 546/114 |

FOREIGN PATENT DOCUMENTS

| | | |
|---|---|---|
| CN | 1840533 | * 10/2006 |
| CN | 101045731 | * 10/2007 |
| CN | 102050829 A | 5/2011 |
| CN | 201180072203.6 | 4/2014 |
| CN | 104817571 A | 8/2015 |
| WO | 2008034912 | * 3/2008 |
| WO | 2011083955 | * 7/2011 |
| WO | WO 2011083955 A2 | 7/2011 |

OTHER PUBLICATIONS

Pan et al., Jingxi Huagong (2006), 23(12), 1221-1226.*
International Search Report in corresponding PCT Application No. PCT/CN2014/095926, dated Oct. 15, 2015.

* cited by examiner

*Primary Examiner* — Niloofar Rahmani
(74) *Attorney, Agent, or Firm* — Leason Ellis LLP

(57) ABSTRACT

This invention provides a new preparation method of Clopidogrel Hydrogen Sulfate spherical crystal form I, using single 2-butanol as solvent, controlling the concentration, addition way and addition speed of sulfuric acid used to salify to shorten the process time, thus separating out Clopidogrel Hydrogen Sulfate from solution system stably with spherality. And the Clopidogrel Hydrogen Sulfate obtained complies with the requirements of the follow-up process on residual solvent, bulk density and mobility.

10 Claims, 5 Drawing Sheets

METHOD FOR PREPARING SPHERICAL CLOPIDOGREL HYDROGEN SULFATE POLYMORPH I

TECHNOLOGY FIELD

Figure 1:
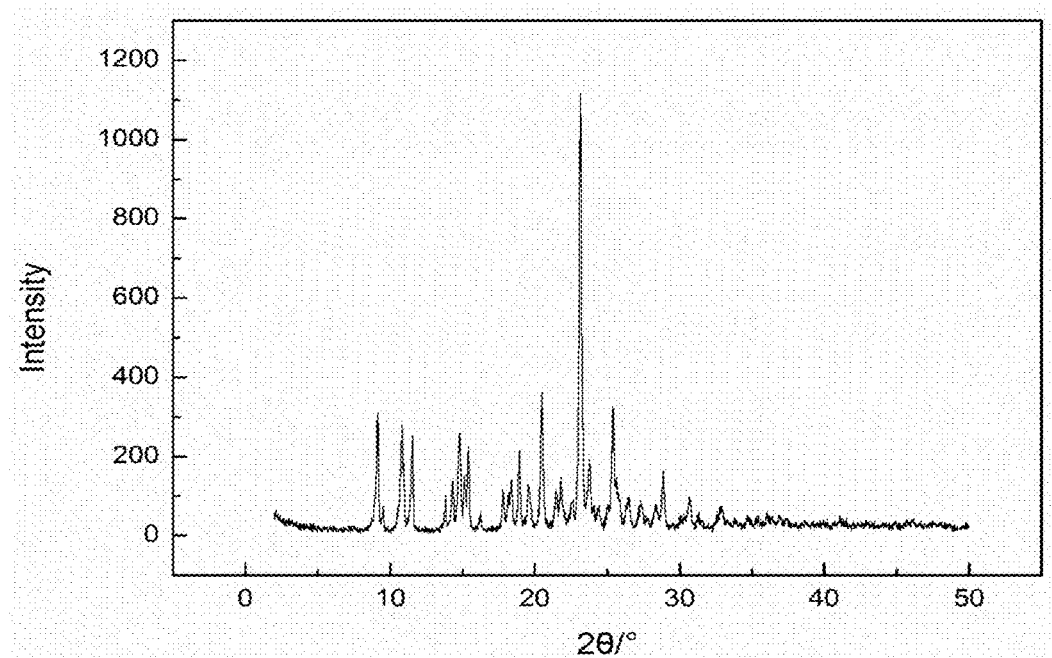

This invention belongs to the field of pharmaceutical synthesis, which specially involves in a method for preparing Spherical Clopidogrel Hydrogen Sulfate crystal form I.

BACKGROUND TECHNOLOGY

Clopidogrel Hydrogen Sulfate (CAS: 135046-48-9) is the sulfate of clopidogrel. Its English name is Clopidogrel Hydrogen Sulfate and chemical name is (s)-α-(2-Chlorophenyl)-6,7-dihydrothieno[3,2-c]pyridine-5(4H) acetate hydrogen sulfate. As an anti-platelet aggregation agent, Clopidogrel Hydrogen Sulfate is developed by Sanofi-aventis in France and marketed firstly in Britain and America in 1998. Clopidogrel Hydrogen Sulfate was marketed in China in 2001, and is clinically used for the prevention of atherosclerosis and thrombosis. At present, Clopidogrel Hydrogen Sulfate preparations in China mainly are Plavix manufactured by Sanofi-aventis and Talcom manufactured by Shenzhen Salubris Pharmaceutical Co., Ltd.

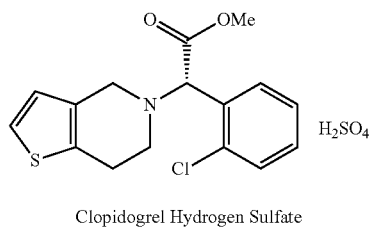

Clopidogrel Hydrogen Sulfate

Clopidogrel Hydrogen Sulfate mainly exist as types I and II crystal form, of which type II is thermodynamic stable crystal and dissolution of corresponding preparation is slightly poor; While type I is thermodynamic unstable crystal form.

Currently, the marketed Clopidogrel Hydrogen Sulfate preparations mostly use type I crystal form, but Clopidogrel Hydrogen Sulfate crystal type I crystal form is not stable in damp and/or hot environment. Therefore, the conventional wet granulation-compressing process is not applicable to Clopidogrel Hydrogen Sulfate preparation, and dry method process is commonly used currently. The Clopidogrel Hydrogen Sulfate powder shows strong static electricity and stickiness, which make it easy to sticking in dry method process, thus to cause unsuccessful production. Although lubricant can avoid sticking, it is reported that conventional alkaline lubricants, such as magnesium stearate, have great effect on the stability of active ingredient, and sticking also occurs while using other conventional lubricants due to low melting point.

One of the feasible programs to solve the issue above is to make active ingredient exist as powder/crystal with good mobility and no electrostatic phenomenon. And current technologies mostly use mixed solvent to prepare spherical Clopidogrel Hydrogen Sulfate crystal form I.

Chinese patent CN201180072203.6 discloses a method for the preparation of spherical Clopidogrel Hydrogen Sulfate crystal form I, using 2-butanol/cyclohexane system to prepare spherical crystallization with size distributions d(0.1)=52.536 μm, d(0.5)=74.567 μm and d(0.9)=106.074 μm. The crystallization improves the mobility of Clopidogrel Hydrogen Sulfate, and reduces electrostatic phenomenon greatly. However, solvent used in this process is 2-butanol-cyclohexane mixture, of which cyclohexane is the solvent of category II enumerated in relevant regulations, such as Guideline for the Study on Residual Solvent of Chemical Drugs, and belongs to solvents required to be restricted for use during drug preparation, and there is strict requirement on its residual; at the same time, mixed solvent brings inconvenience in the recovery and utilization of the solvent. In addition, one of the critical technical factors of this process is that sulfuric acid and cyclohexane solution shall be added slowly into solvent system under cooling condition, which makes this process complex, and cyclohexane may change color due to the addition of concentrated sulfuric acid, thus affects quality of product; moreover, this process needs longer time, which, on one hand, has risk of crystal form transformation, on the other hand reduces the bulk density of product. Patent WO2011083955 discloses a method for the preparation of Clopidogrel Hydrogen Sulfate spherical crystallization, of which the solvent used to prepare spherical crystallization in example 5 is 2-butanol-water mixture. But water, used in solvent of this process, has a high boiling point, it needs longer time and higher temperature to be removed in the follow-up process; In addition, water also goes against the generation crystal form. Yield of this process is just 53% which is in a lower level. In the comparison example 1 of this patent, it studies the effect of usage amount of water on product modality, and the result shows that single 2-butanol solvent system is not in favor of the formation of spherical crystallization and Clopidogrel Hydrogen Sulfate obtained is disorganized powder as shown in patent FIG. 4. Therefore, to search a Clopidogrel Hydrogen Sulfate spherical crystallization I of environmentally friendly, low cost, high yield and whose character meets the requirements of the follow-up preparation process, is still a technical issue not solved with available technologies.

Introduction To the Invention

The invention aims to overcome the deficiency of current technologies, and provides a new preparation method of spherical Clopidogrel Hydrogen Sulfate crystal form I. This method uses single 2-butanol as solvent, by controlling the concentration, addition way and addition speed of sulfuric acid used to salify, the process time is shortened and Clopidogrel Hydrogen Sulfate can be crystallized stably as sphere from solution. And the Clopidogrel Hydrogen Sulfate obtained meets the requirements on residual solvent, bulk density and mobility in follow-up process.

The benefits above of this invention are achieved by the following technical proposal.

A method for the preparation of Clopidogrel Hydrogen Sulfate crystal form I, the method mentioned includes the following steps:

(1) Dissolve clopidogrel free alkali into 2-butanol to obtain free alkali solution with concentration 0.02~0.1 g/mL. Rapidly add 2-butanol solution with sulfuric acid 0.5~2.0 mol/L at 0~35° C., and the molar ratio of sulfuric acid and clopidogrel free alkali added is 0.8~1.1:1;

(2) Keep the temperature in step (1), add Clopidogrel Hydrogen Sulfate crystal form I with mass ratio to clopidogrel free alkali 1~10 wt % as crystal seeds, and keep the temperature and stir for 4~8 h;

(3) Filtrate, wash and dry to obtain Clopidogrel Hydrogen Sulfate spherical crystal form I; It's characterized by that the addition time of sulfuric acid and 2-butanol solution in step (1) is controlled within 40 min.

In step (1), addition period of time of sulfuric acid is the key of this process. In Chinese patent CN201180072203.6, add sulfuric acid and cyclohexane solution slowly within 8~10 hours (Example 1). It is observed, in the repeated studies, that quasi-emulsion droplet is firstly formed in the solution system, then conglomerate to be spherical crystallization. For this method, if the addition of sulfuric acid is too slow, the generated Clopidogrel Hydrogen Sulfate crystal form I has a tendency to transform into crystal form II with time passing, and bulk density of the spherical crystallization obtained has a dramatic decline; If the addition of sulfuric acid is too fast, gelatinization will occur to affect the crystallization. While the inventor wondrously finds that when single 2-butanol recrystallization solvent is used, the crystallization goes in different crystal process, in detail, if the addition of sulfuric acid is controlled within 40 min, it is in favor of the generation of spherical crystal form I. Possibly fast addition of sulfuric acid is in favor of the generation of higher degree of super-saturation, which improves the nucleation and growth speed of crystal, and then nucleates and grows fast into relative pyknotic sphere. Clopidogrel Hydrogen Sulfate obtained is spherical crystal form I, and its bulk density and form meet the requirements of the follow-up process, and yield is relatively high. It also finds, in the study, that product bulk density declines correspondingly and the appearance tends to be bad with time prolonging on the premise that the product is ensured to be spherical and single crystal form. In one embodiment, bulk density and spherical crystal form are both better, if the addition of sulfuric acid is controlled within 20 min. In one embodiment, the evaluation of comprehensive bulk density and spherical crystal form are the best, if the addition time of sulfuric acid is controlled within 10 min. The addition of sulfuric acid mentioned is common in prior art, such as adding at constant speed, adding in portions, etc. Due to shortening the addition time of sulfuric acid, the time for one batch using method in this invention is also shortened greatly. In detail, time of the process in this invention is within 10 hours, but it is generally 20~30 hours for current technologies; Molar ratio of sulfuric acid and clopidogrel free alkali added is 0.8~1.1:1, 0.95~1.05:1 is preferred; And the preferred purity of clopidogrel alkali is more than 95%.

In step (2), due to the special crystal process, sulfuric acid adding into the system should be diluted, and the concentration of sulfuric acid in 2-butanol is 0.5~2.0 mol/L. The preferred concentration of sulfuric acid in 2-butanol is 0.6~1.0 mol/L; the concentration of free alkali solution affects the product in some degree, although the increase in concentration can improve the yield in some degree. However, we find that over-high concentration makes crystal transform easily, bulk density of the product obtained has a trend to reduce and the products obtained do not meet the requirements of the follow-up preparation; while over-low concentration makes slowly nucleation and growth and leads a low yield. The inventor finds that when the concentration of free alkali solution is 0.02~0.1 g/mL and the preferred concentration is 0.040~0.065 g/mL, it is in favor of the generation of spherical crystal.

Step (1) mentioned can be achieved at 0~35° C., and the preferred temperature is 10~30° C. In the method of this invention, the addition of crystal seed contributes to the generation of spherical crystal. Clopidogrel Hydrogen Sulfate crystal form I is used as crystal seed in this invention. The inventor finds that the mass ratio of clopidogrel free alkali and quantity of crystal is 1~10 wt % and the preferred is 1~5 wt %, it helps the crystal separate out rapidly as stable and uniform sphere.

Step (2) can be conducted in the temperature range of step (1) which is at 0~35° C. The properties of Clopidogrel Hydrogen Sulfate is special, which is shown that over-high temperature causes crystal form transformation, so that product is obtained as mixed crystal form; while over-low temperature is not in favor of nucleating and growth of crystal and yield is also low, which increases production cost. Temperature is preferred to be controlled at 10~30° C.; For more preferred, to make product form, bulk density and yield reach the optimization, the temperature can have somewhat fluctuation during manufacturing, and it can choose gradual reduction and also step reduction, in one embodiment, reduce temperature for further crystallization after keeping at higher temperature for a certain time; or conduct by two steps: keep at 20~30° C. for 2~4 hours and then cool to 10~20° C., and stir for further crystallization.

Single 2-butanol solvent is used in the method of this invention. 2-butanol is the solvent of category III enumerated in relevant regulations, such as Guideline for the Study on Residual Solvent of Chemical Drugs, and it has less strict requirements to the residual; In addition, this spherical crystal is obtained by spherical growth mechanism, but not spherical coalescence mechanism mentioned in current technologies. Therefore, it, to a great degree, reduces the absorption of solvent during the growth course of crystal, which makes removing of solvent easier in follow-up process and residual solvent is relatively easy to reach the requirements of the follow-up manufacturing process.

In commercial process, clopidogrel free alkali mentioned in former technical proposal, can be prepared by corresponding clopidogrel salt, and the steps are as below:

(1) Dissolve clopidogrel salt in organic solvent;
(2) Adjust pH value of the system with alkali, wash the organic phase with a little water and remove the water in the organic phase by dehydrating agent;
(3) Concentrate organic phase in vacuum to obtain clopidogrel free alkali;

In step (1), clopidogrel salt is preferred one or mixture of more than one in various amounts of disulfate, camphorsulfonates and hydrochloride, skilled person know that the more the purity of clopidogrel salt is, the better for the preparation of spherical crystal. It is preferred that the purity of clopidogrel salt is above 95%; organic solvents are solvents immiscible with water, and the organic solvent is preferred selected from one or mixture of more than one in various amounts of dichloromethane, chloroform, ethyl acetate.

In step (2) of the proposal that includes the preparation of Clopidogrel Hydrogen Sulfate free alkali: the purpose of using alkali to adjust pH value is to make Clopidogrel Hydrogen Sulfate turn into clopidogrel base, so that organic solvent can be used for extraction. This operation can be conducted by adding solid alkali or aqueous alkali after water is added; The alkali can be those generally used by skilled person, such as sodium carbonate, sodium bicarbonate, potassium carbonate, potassium bicarbonate, sodium hydroxide, potassium hydroxide, etc. The dehydrating agent mentioned can be those generally used by skilled person, such as anhydrous magnesium sulfate, anhydrous sodium sulfate, etc.

To achieve continuous production in industrial, it can combine with the above-mentioned preparation steps of clopidogrel free alkali and Clopidogrel Hydrogen Sulfate spherical crystal form I to obtain the following proposal complying with continuous production in industrial:

A method for the preparation of Clopidogrel Hydrogen Sulfate spherical crystal form I includes the following steps:
(1) Dissolve clopidogrel salt into organic solvent;
(2) Adjust pH value of the system with alkali, wash the organic phase with a little water and remove the water in the organic phase by dehydrating agent;
(3) Concentrate organic phase in vacuum to obtain clopidogrel free alkali;
(4) Dissolve clopidogrel free alkali obtained in step (3) in 2-butanol to get a free alkali solution with concentration 0.02~0.1 g/mL, rapidly add 2-butanol solution containing 0.5~2.0 mol of sulfuric acid at 0~35° C., and the molar ratio of sulfuric acid and clopidogrel free alkali is 0.8~1.1:1;
(5) Keep the same temperature range as step (4), add Clopidogrel Hydrogen Sulfate crystal form I with mass ratio to clopidogrel free alkali 1~10 wt %, keep the temperature and stir for 4~8 h;
(6) Filtrate, wash and dry to get Clopidogrel Hydrogen Sulfate spherical crystal form I; It's characterized by that the addition time of sulfuric acid-2-butanol solution in step (1) is controlled within 40 min.

This method includes the preparation steps of clopidogrel free alkali and Clopidogrel Hydrogen Sulfate spherical crystal form I; and in these steps, all technical feature, range, contents referred and relevant optimized/preferred range are correspondingly the same to the above-mentioned Clopidogrel Hydrogen Sulfate spherical crystal form I technical proposal and clopidogrel free alkali technical proposal.

Methods mentioned in this invention all can prepare Clopidogrel Hydrogen Sulfate crystal with regular sphere, which can be observed directly by common observational methods, such as scanning electron microscope (SEM), microscope, etc. Further observation to the form finds that size distribution of spherical crystal can be 40 um≤d(0.1)≤60 um, 60 um≤d(0.5)≤90 um and 90 um≤d(0.9)≤150 um, which are much homogeneous. Crystal of this form can improve preparation properties and dissolution rate to a certain degree.

It finds that, by X-ray powder diffraction method, Clopidogrel Hydrogen Sulfate prepared by the method mentioned in this invention shows diffraction peaks when 2θ is 9.22±0.02°, 10.90±0.02°, 11.58±0.02°, 13.84±0.02°, 14.40±0.02°, 14.82±0.02°, 15.54±0.02° or 23.16±0.02°. For a further comparison, Clopidogrel Hydrogen Sulfate spherical crystal prepared by the method mentioned in this invention is crystal form I. Common test methods in prior art also can be used for the spherical crystal form mentioned, such as differential scan calorimeter (DSC), fourier-transform infrared (FT-IR), etc.

The Clopidogrel Hydrogen Sulfate spherical crystal prepared by method mentioned in this invention meet the requirements of the follow-up preparation process. In detail, the spherical crystal mentioned reaches the presupposed purpose, that is, to improve mobility and reduce electrostatic phenomenon. Mobility is reflected by powder angle of repose, and use the common test methods to test powder mobility, such as fixed-funnel method; and electrostatic phenomenon can be reflected by bulk density, and use the common test methods to test powder bulk density, such as measuring-cylinder-knocking method.

This invention has the following advantages and benefits compared with the current technology:
1. To overcome the technical difficulty that single solvent is difficult to prepare spherical crystal, use single solvent 2-butanol to prepare Clopidogrel Hydrogen Sulfate spherical crystal form I and reduce solvent residual risk and cost for recovering;
2. The spherical crystal obtained has higher mobility and bulk density, which can meet the requirements of the follow-up preparation process (such as direct compression) with high requirements.
3. Product preparation can realize industrialization continuous production.

INSTRUCTIONS FOR FIGURES

Figure 2:
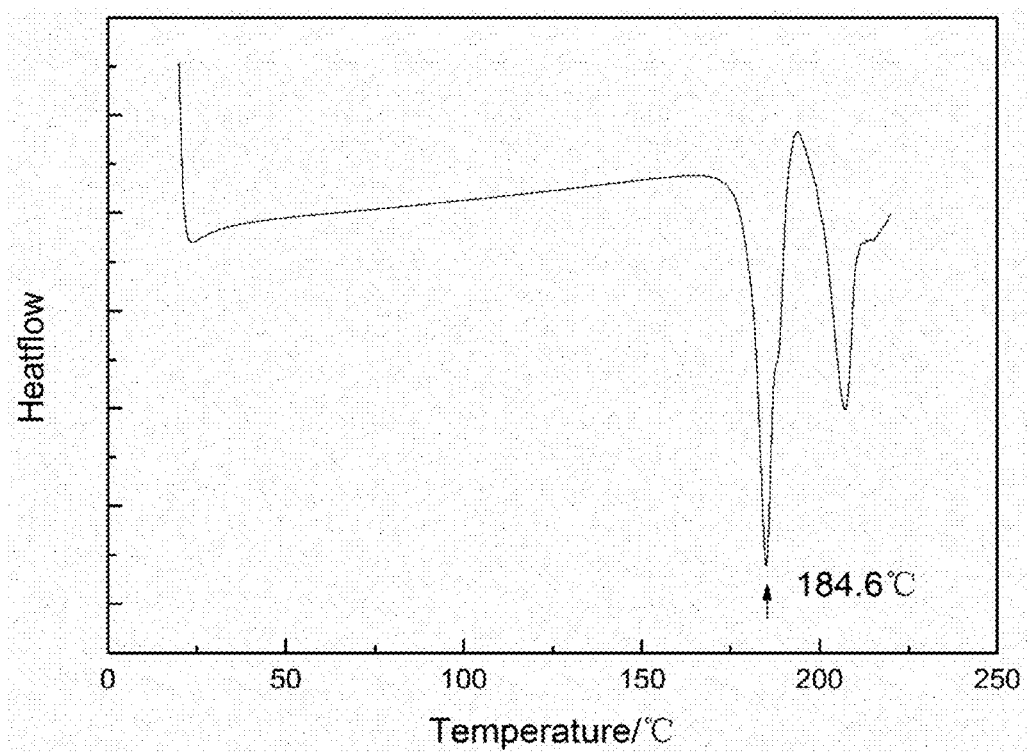
Figure 3:
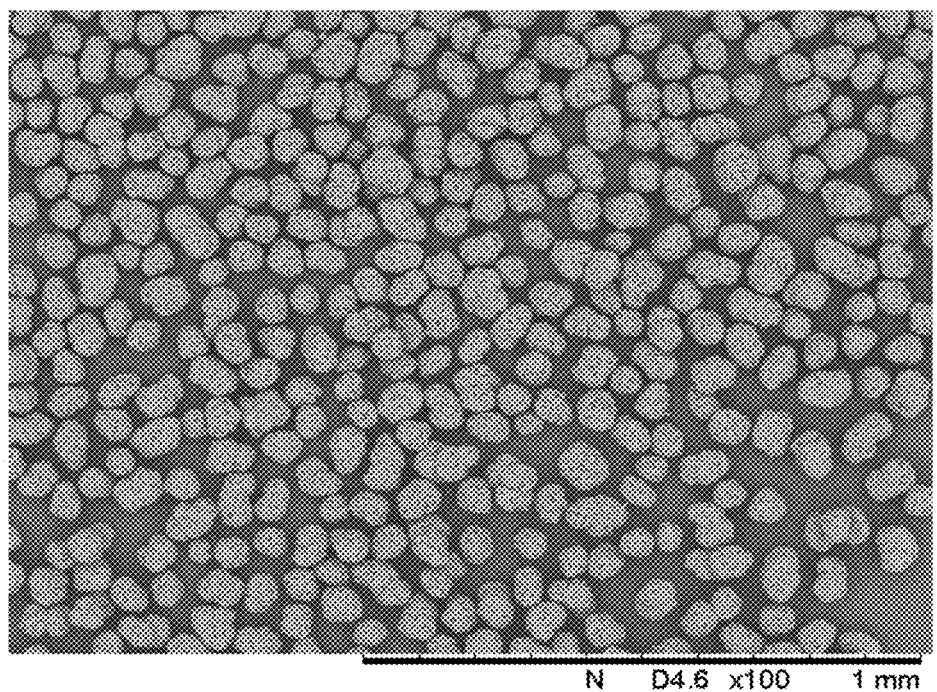
Figure 4:
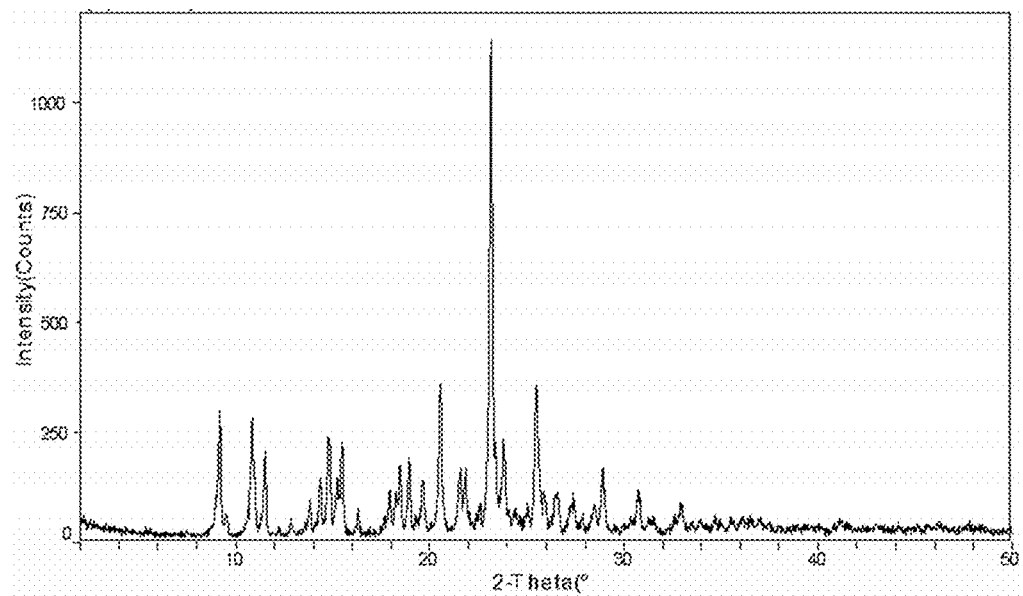
Figure 5:
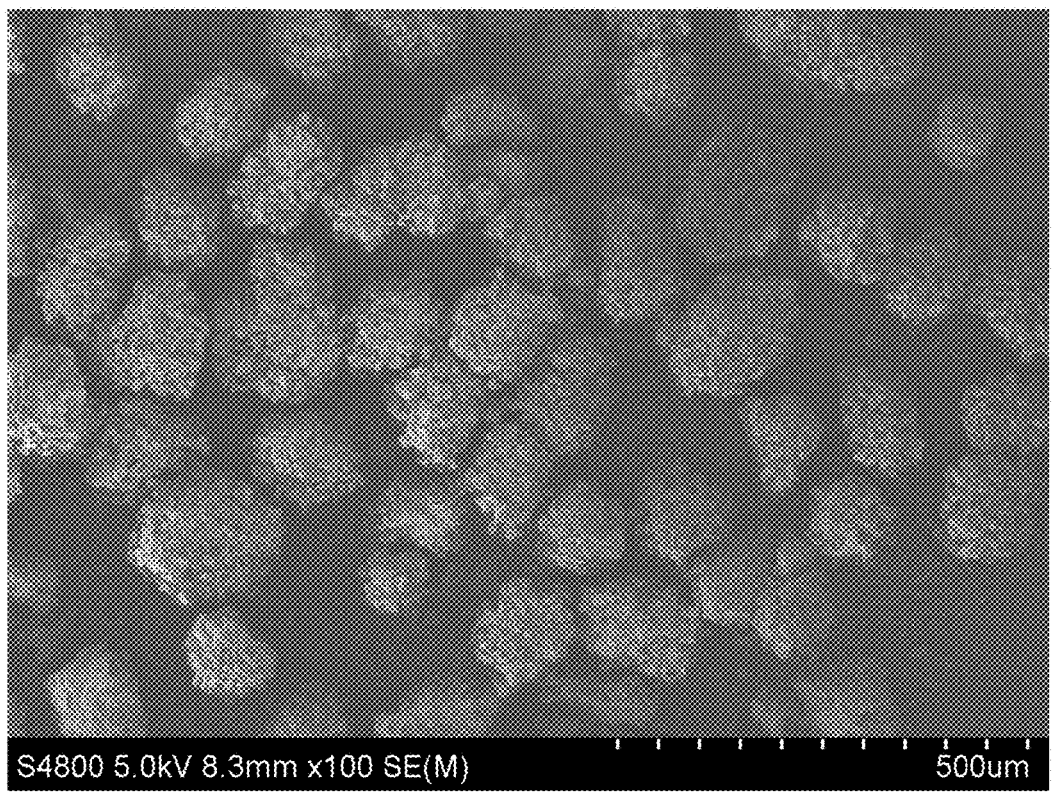

FIG. 1 Clopidogrel Hydrogen Sulfate XRPD spectrogram obtained in example 1
FIG. 2 Clopidogrel Hydrogen Sulfate DSC spectrogram obtained in example 1
FIG. 3 Clopidogrel Hydrogen Sulfate SEM picture obtained in example 1
FIG. 4 Clopidogrel Hydrogen Sulfate XRPD spectrogram obtained in comparison example 1
FIG. 5 Clopidogrel Hydrogen Sulfate SEM picture obtained in comparison example 1

SPECIFIC MODE OF EXECUTION

Further describe this invention combined with the following execution examples and figures, but mode of execution is not limited to it.

EXAMPLE 1

Dissolved 760 g of clopidogrel hydrosulfate weighed (Purity>99.0%) into the mixing solution of 10 L of dichloromethane and 5 L of water, added solid sodium bicarbonate to water phase till pH>7. Kept still, washed the organic phase with water (1 L×2), and removed water with anhydrous magnesium sulfate till the solution was clear.

Filtrated the organic phase and evaporated in vacuum rotary evaporator till the mass didn't change. Dissolved the residuum in 10.5 L of 2-butanol, and kept the solution at 25° C. Dissolved 100 ml of concentrated sulfuric acid (181 g) in 2.5 L of 2-butanol, added into the system within 10 min, and dispersed 10 g of crystal form I into 1 L of 2-butanol, and added mixture into the system together. Kept it at 25° C. for 2.5 h, reduced the temperature to 15° C. and kept for 3 h. Performed suction filtration, washed filter cake with ethyl acetate, vacuum drying at 40° C. for 1.0 h to get 610 g of the product (residual 2-butanol<0.2%).

XRPD spectrogram of the product obtained was as shown in FIG. 1, DSC spectrogram was as shown in FIG. 2 and SEM picture was as shown in FIG. 3.

EXAMPLE 2

Added 1000 g of clopidogrel camphorsulfonates (Purity>99.0%) into the mixing solution of 10 L of dichloromethane and 5 L of water, added solid sodium bicarbonate to water phase till pH>7. Kept still, washed the organic phase with water (1 L×2), and removed water with anhydrous magnesium sulfate till the solution was clear.

Filtrated the organic phase and evaporated in vacuum rotary evaporator till the mass didn't change. Dissolved the residuum into 10.5 L of 2-butanol, and kept the solution at 25° C. Dissolved 100 ml of concentrated sulfuric acid (181 g) into 2.5 L of 2-butanol, added mixture into the system within 10 min, and dispersed 12 g of crystal I into 1 L of 2-butanol, and added into the system together. Kept at 25° C.

for 2.5 h, reduced the temperature to 15° C. and kept for 3 h. Performed suction filtration, washed filter cake with ethyl acetate, vacuum drying at 40° C. for 1.0 h to get 605 g of the product (residual 2-butanol<0.2%). It is tested to be Clopidogrel Hydrogen Sulfate spherical crystal form I.

COMPARISON EXAMPLE 1

Dissolved 760 g of clopidogrel hydrosulfate (Purity>99.0%) in the mixing solution of 10 L of dichloromethane and 5 L of water, added solid sodium bicarbonate to water phase till pH>7. Kept still, washed the organic phase with water (1 L×2), and removed water with anhydrous magnesium sulfate till the solution was clear.

Filtrated the organic phase and evaporated in vacuum rotary evaporator till the mass didn't change. Dissolved the residuum into 10.5 L of 2-butanol, and kept the solution at 25° C. Dissolved 100 ml of concentrated sulfuric acid (181 g) into 2.5 L of 2-butanol, added into the system within 10 min, and dispersed 10 g of crystal I into 1 L of 2-butanol, and added the mixture into the system together. Kept at 25° C. for 2.5 h, reduced the temperature to 15° C. and kept for 3 h. Performed suction filtration, washed filter cake with ethyl acetate, vacuum drying at 40° C. for 1.0 h to get 608 g of the product (residual 2-butanol<0.2%). XRPD spectrogram of the product obtained was as shown in FIG. 4, and SEM picture was as shown in FIG. 5. Seen from FIG. 4, the product obtained was the mixture of Clopidogrel Hydrogen Sulfate crystal forms I and II, and seen from FIG. 5, the product form existed as irregular sphere.

EXAMPLE 3

Used the same ratio and operation as example 1, but different addition time of sulfuric acid to study the relationship between addition time of sulfuric acid and product form and crystal form.

| No. | Time (min) | Form | Crystal form | Bulk density |
|---|---|---|---|---|
| 1 | 15 | Spherical | Form I | 0.77 |
| 2 | 20 | Spherical | Form I | 0.76 |
| 3 | 30 | Spherical | Form I | 0.75 |
| 4 | 40 | Spherical | Form I | 0.75 |
| 5 | 80 | Spherical-like | Mixed crystal form I/II | 0.68 |
| 6 | 120 | Spherical-like | Mixed crystal form I/II | 0.65 |
| 7 | 180 | Spherical-like | Mixed crystal form I/II | 0.58 |

As can be seen, on the premise other process condition was same, addition time of sulfuric acid related with product form and crystal form. In detail, as addition time of sulfuric acid was prolonged, the product showed a crystal transformation tendency and this tendency increased as time was prolonged. And the product obtained was mixed crystal form when the additional time was prolonged to be more than 40 min It also observed in the study that as addition time of sulfuric acid was prolonged, bulk density of the product reduced correspondingly, form changed as well and became bad uniformed. When the addition time of sulfuric acid was controlled within 20 min, bulk density and form were better; when the addition time of sulfuric acid was controlled within 10 min, evaluation of comprehensive yield, bulk density and form was optimized.

EXAMPLE 4

Used Malvern-3000 granulometer to test the form and homogeneity of products obtained in examples 1 and 2, and the test results were as shown in the following table:

| Form | d(0.1) | d(0.5) | d(0.9) |
|---|---|---|---|
| Example 1 Spherical | 58.24 μm | 70.67 μm | 113.10 μm |
| Example 2 Spherical | 46.46 μm | 62.48 μm | 90.60 μm |

As can be seen, the Clopidogrel Hydrogen Sulfate spherical crystals obtained in examples 1 and 2 had a homogeneous form. A further test of preparation dissolution found that the dissolution rate of the preparation prepared by the spherical crystal in this invention was faster than that of marketed products.

EXAMPLE 5

Tested respectively the angle of repose and bulk density of products obtained in examples 1 and 2 by using fixed-funnel method and measuring-cylinder-knocking method, and the test results were as shown in the following table:

| | Angle of repose (°) | Bulk density (g/ml) |
|---|---|---|
| Example 1 | 28 | 0.78 |
| Example 2 | 30 | 0.77 |
| Power | Regular and uniform sphere | Regular and uniform sphere |

As can be seen, angles of repose in examples 1 and 2 were all between 25°~32°, so the mobility of spherical crystals obtained was far superior to powder product;

Bulk density of examples 1 and 2 was between 0.75 and 0.80 g/ml, which was far higher than the powder product, so the electrostatic effect of the spherical crystals obtained reduced greatly.

In conclusion, the spherical crystal obtained in this invention was more complied with the commonly used preparation process of current technology of Clopidogrel Hydrogen Sulfate and would contribute to further improvement of the process.

A further scale-up study showed that the process to prepare Clopidogrel Hydrogen Sulfate spherical crystal form I in examples 1~3 had the same effect to the execution example when used in large scale production, so the corresponding process was applicable to large-scale production as well.

The execution examples above are better mode of execution of this invention, but not limited by the execution examples, and any changes, ornament, replacement, combination and simplification without violation the spirit and principle of this invention shall be all equivalent substitute mode, and included in the protection range of this invention.

The invention claimed is:

1. A method for preparing Clopidogrel Hydrogen Sulfate spherical crystal form I, the method comprising the following steps:
   (1) Dissolving clopidogrel base in 2-butanol as a single solvent to produce a first solution having a clopidogrel base concentration of 0.02~0.1 g/mL, adding at 0~35° C. to the first solution a solution of sulfuric acid in 2-butanol to produce a second solution, wherein the solution of sulfuric acid in 2-butanol has a sulfuric acid concentration of 0.5~2.0 mol/L, wherein the molar ratio of sulfuric acid to clopidogrel base is 0.8~1.1:1, wherein the solution of sulfuric acid in 2-butanol is added to the first solution within 40 minutes;
   (2) adding seed Clopidogrel Hydrogen Sulfate crystal form I to the second solution, wherein the seed Clopidogrel Hydrogen Sulfate crystal form I is in an amount ranging from 1 wt % to 10 wt % of the clopidogrel base, and stirring for 4~8 h; and (3) filtrating, washing and drying to obtain Clopidogrel Hydrogen Sulfate spherical crystal form I.

2. The method of claim 1, wherein in step (1) the solution of sulfuric acid in 2-butanol is added to the first solution within 20 min.

3. The method of claim 1, wherein the solution of sulfuric acid in 2-butanol has a sulfuric acid concentration of 0.6~1.0 mol/L.

4. The method of claim 1, wherein the first solution has a clopidogrel base concentration of 0.040~0.065 g/mL, and wherein the molar ratio of sulfuric acid to clopidogrel base is 0.95~1.05:1.

5. The method of claim 1, wherein in step (1) the solution of sulfuric acid in 2-butanol is added to the first solution within 10 min.

6. The method of claim 1, wherein in step (1) the solution of sulfuric acid in 2-butanol is added to the first solution at 10~30° C.

7. The method of claim 1, wherein step (2) further comprises a step of maintaining a temperature at 20~30° C. for 2-4 h, then cooling to 10-20° C. after the adding step and before the stirring step.

8. The method of claim 1, wherein the of Clopidogrel Hydrogen Sulfate crystal form I is in an amount ranging from 1 wt % to 5 wt % of the clopidogrel base.

9. The method of claim 1, further comprising a step of preparing clopidogrel base comprising the sub-steps of:
(a) dissolving a clopidogrel salt in one or more organic solvents to produce a third solution;
(b) adjusting pH value of the third solution with an aqueous alkaline solution, washing an organic phase with water, and removing water in the organic phase by one or more dehydrating agents;
(c) concentrating the organic phase in vacuum to obtain clopidogrel base.

10. The method of claim 9, wherein in step (a), the clopidogrel salt is selected from the group consisting of a disulfate, a camphorsulfonate, a hydrochloride, and mixtures thereof; wherein the organic solvent is selected from the group consisting of dichloromethane, chloroform, ethyl acetate, and mixtures thereof; wherein in step (b), the aqueous alkaline solution comprises sodium carbonate, sodium bicarbonate, potassium carbonate, potassium bicarbonate, sodium hydroxide, and/or potassium hydroxide; wherein the dehydrating agent is selected from the group consisting of anhydrous magnesium sulfate, anhydrous sodium sulfate, and a mixture thereof.

* * * * *